United States Patent [19]
Soumillion et al.

[11] Patent Number: 6,143,880
[45] Date of Patent: Nov. 7, 2000

[54] PIG MYOGENIN GENE AND METHOD TO IDENTIFY POLYMORPHISMS RELATED TO MUSCLE GROWTH

[75] Inventors: Ann Elisabeth Soumillion, Maaseik, Belgium; Marinus Frederik te Pas, Putten, Netherlands

[73] Assignees: Cofok B.V., Oosterhout; Beheermaatschappij Varkensverbetering Zuid B.V., Vught; ID-DLO, Lelystad, all of Netherlands

[21] Appl. No.: 09/091,899
[22] PCT Filed: Dec. 20, 1996
[86] PCT No.: PCT/NL96/00497
§ 371 Date: Oct. 2, 1998
§ 102(e) Date: Oct. 2, 1998
[87] PCT Pub. No.: WO97/23644
PCT Pub. Date: Jul. 3, 1997

[30] Foreign Application Priority Data

Dec. 22, 1995 [EP] European Pat. Off. ............... 95203623

[51] Int. Cl.[7] .................... C07H 21/04; C07H 21/02; C12Q 1/68; C12P 19/34
[52] U.S. Cl. .................... 536/24.31; 536/23.1; 536/23.5; 536/24.33; 435/6; 435/91.2
[58] Field of Search ..................... 435/6, 91.2; 536/23.5, 536/24.31, 24.33, 23.1

[56] References Cited

PUBLICATIONS

Briley, G.P. et al. Animal Biotechnology 6(2):79–92, Dec. 1995.
Te Pas M.F.W. et al. J. Anim. Breed. Genet. 111:404–412, 1994.
GenEmbl Accession No. U14331, Dec. 1994.
Ahern, H. The Scientist 9(15):20, Jul. 1995.

Primary Examiner—Carla J. Myers
Assistant Examiner—Diana Johannsen
Attorney, Agent, or Firm—Trask Britt

[57] ABSTRACT

A novel sequence of the pig myogenin gene and methods of using the myogenin gene and its products. Also disclosed are methods for detecting different alleles of the pig myogenin gene, which different alleles are associated with differences in the genotypic and/or phenotypic traits of the pigs having those alleles. Methods for distinguishing between alleles resulting in different phenotypes, particularly using techniques involving selective amplification of pig myogenin gene derived materials are also disclosed. These techniques are especially suitable for selecting animals to be used in breeding programs. Breeding programs employing such techniques are also disclosed.

1 Claim, 5 Drawing Sheets

FIG. 1

```
  GATCTTTTTTAAGAGAGTCTCATCTGACTGACACAGTCTGGGTAAGGTGCTGTGAGGAAGCAGGGGGATGCATAAACTGACTTCTCCAGGCCCCTTCCAGCCTACACCTACCCCTTCCTTCTTCCC
  CCCCGCCTCACCCCACCCCCCAC  150
        E3
  TGGGCTTCTTTGGGACTGGCGAGTAGGCAGGCCGCCAGCTAGGAGTAATTGAAAGGA...AGATGAGAGAGAATGTGTGTCTCCCCACCTCCCCCAGCCCCCATGGGGCTGCAGAGAAATGA
  AAACTAATCAAATTACACCCTATGG  300
               E2
  CCTCCTTACCCGTGCACAGGAGCCTGCTGGGGGCAGGCTGGCTGTGGGGAGGGGGGTGCAGGGGGAGGGGGAGAGGGGAATCACATCTAATCACTGTAAACGTCTTGATGTGCAGCAACAGCTT
  AGAGGGGGCTCAGGTTTCTGTGGC  450
  GTTGGGCTATATTTATCTCTGGTTCCATGCCAGCGGGGAGGGTTTAAATGGCACCCAGCAGTTGGCCTGCGTGAGGGCTGCAGGAGCTTGGGGGCTGGTGGCAGGAACAAGTCTTTTCTGACCCCATGGA
  GCTGTATGAGACATCCCCCTACTT  600     TATA             M  E  L  Y  E  T  S  P  Y  F  10
  2  MEF-2   NF-1     E1
  CTACCAGGAACCCCACTTCTATGACGGGGAAAACTACCTGCCCGTCCACCTCCAGGGCTTTGAGCCACCAGGCTACAGCGGACTGAGTCTGAGCCCTGAGGCCCGAGTGCCCTGGAAG
  ATAAGGGGCTGGGGACCCCCGAGCA  750
  2  Y  Q  E  P  H  F  Y  D  G  E  N  Y  L  P  V  H  L  Q  G  F  E  P  P  G  Y  E  R  T  E  L  S  L  S  P  E  A  R  V  P  L  E  D  K  G  L  G  T  P  E  H   60
  CTGCCCCAGGCCAGTGCCTGCTGCGTGGGCATGTAAGGTGTGTAAGAGGAAGTCCGTGTCTGTGGACCGTCGGCGGCCGCCACGTGAGGGAGAAGCGCAGGCTCAAGAAGGTGAATGAGGCCTTTG
  AGGCCCTGAAGAGAGACACCCTGCT  900
  2  C  P  G  Q  C  L  P  W  A  C  K  V  C  K  R  K  S  V  S  V  D  R  R  R  A  A  T  L  R  E  K  R  R  L  K  K  V  N  E  A  F  E  A  L  K  R  S  T  L  L   110
  CAACCCCAACCAGCGGCTGCCAAGGTGGAGATCTCTGCGCAGCGCCATCCAGTACATCGAGCGCCTGCAGGCCCTGCTCAGCTCCTCAACCAGGAGGAGCGAGACCTCCGCTACCGAGGCGGGG
  GCGGGCCGCAGCCAGGGtaagtgg   1050
  2  N  P  N  Q  R  L  P  K  V  E  I  L  R  S  A  I  Q  Y  I  E  R  L  Q  A  L  L  S  S  L  N  Q  E  E  R  D  L  R  Y  R  G  G  G  P  Q  P  G   157
  1 ctgtccaccccccgccctggggtcggggggcaggaggcaccagacagccctggggtaccctgagatggggagaacaggagccaggcaggtctgagaaggcttcaaggtgcctgccctttgagcgcttgtagagcggggg1200
  1 gcccagctgacctctgcgctgccaccgtgtcctttcagataaggcagtgggggaggagcctgggggaggggggggcacagagcaaggcaggaaggatccaggagagcaagtccgatggagctgaggagctgatgaggagaagattcaccccg 1350
  1 tgtctggggacaggggctaaaaggcaaggccaaagtccgtgaagaagactgctttcccccaccgaccccatctgaggtatggcgagcagacagaatgccacccagaactgaggtcgcagcagcagcacctgggtgttgaggaccagacaccctgaagcagaggtctgtggcctgacagagtttgg 1500
  1 tggacattcgccttcctcattcgcctcctatccaggtcagggatcaggcagagggaccccctaagctgaagtgaggtcagacttgtagtgggtcagacttgtgtcaccttcaaccccaccaccaggtgctctgccattggagaccagcaggttgtggcctagaacagcggagcgagcctg 1650
  1 gcattgaaaggagctgatttgaagattcgtgaatagggagggggggggctggacaggaggggtccttgagacgtggaactgtaagagcagcagacactgcctaagaacagcaggagccctg 1800
  1 acctlggggcttcaccatctgagGTGCCCCAGTGAATGCAGTTCCCACAGCGCCTCCTGCAGTCCAGTGGGGCAGTTCGCACTGAGTTCGCCCCAACCCAGGGGtaagtgaggaggccaggaccctgtacctgacttaagccc 1950
  2       V  P  S  E  C  S  S  H  S  A  S  C  S  P  E  W  G  S  A  L  E  F  G  P  N  P  G   184
  1 acagtctatctgaggtcagttcccctcttaccttaccccgtcccttgcctctcttcccctgcctcttagggaccctctaggaggcacaaacagtgagctgagctgagctgaagaagccctgaagcctgaccagctaagg 2100
```

PIG MYOGENIN GENE AND METHOD TO IDENTIFY POLYMORPHISMS RELATED TO MUSCLE GROWTH

PRIORITY CLAIM

This application is the national phase of international application PCT/NL96/00497, filed Dec. 20, 1996.

TECHNICAL FIELD

The invention relates to the field of molecular biology as well as to the field of breeding methods for farm animals, in particular pigs. In particular the invention relates to the use of diagnostic methods derived from the field of molecular biology in breeding programmes that select animals on production traits that improve their breeding value.

BACKGROUND

By selecting animals on their breeding value calculated mainly from phenotypic measurements of production traits, breeding has greatly improved the genotype for production traits of livestock animals. Thus, traditionally, breeding programmes have selected for phenotypic characteristics of animals. However, more recently selection for genotypic characteristics that are associated with improved production traits have gained interest in the field. Selection for phenotypic characteristics entails mainly selection of the offspring or siblings or other relatives of the animals to be selected whereas selection of specific genotypic characteristics allows for earlier and specific detection of animals of interest.

Within methods that select on specific genotypic characteristics, one may distinguish between methods that detect genetic variation in genes or quantitative trait loci that are merely associated with production traits of animals and methods that detect genetic variation in functional genes that directly influence those production traits. One of the former methods is a marker assisted selection wherein polymorphisms in markers identified in a random manner are associated with production traits.

For instance, meat production is closely linked to embryonic muscle formation. Biologically, production is concentrated in defined tissues of the animal, e.g. muscle tissue for lean meat production. In breeding programmes for optimizing porcine lean meat production, various levels of selection pressure have been applied to different tissues (i.e. muscle, fat and bone).

Muscles are complex tissues composed of a number of different cell types, e.g. myocytes (the most predominant) consisting of myofibres and satellite cells, intramuscular adipocytes, fibroblasts, endothelial cells, neurocytes, etc. Handel and Stickland (1984, 1988) showed that the number of myofibres present at birth determines the maximal lean meat growth capacity of pigs. Double-muscled cattle show a higher number of prenatally developed myofibres than other cattle (Swatland and Kiefer 1974; Hanset et al., 1982), which suggests that lean meat production capacity is determined by the embryonic development of myocyte number.

Myogenesis is a complex, multistep process that chronologically involves:
(1) Progenitor cell determination to the myogenic lineage.
(2) Migration of myogenic stem cells (myoblasts) to appropriate locations in the early embryo.
(3) Proliferation of myoblasts and non-myogenic muscle-tissue cells.
(4) Terminal myocyte differentiation (i.e. fusion of myoblasts) and expression and organization of specific gene products active only in terminally differentiated muscle cells.
(5) Maintenance of the terminal differentiated state and modulation of myofibres in various myofibre types in response to age and physiological cues (Edgerton and Roy, 1991; Funk et al., 1991; Gunning and Hardeman, 1991; Olson, 1992).

A model based on the action of the MyoD gene-family describes a mechanism for the genetic regulation of myogenesis. There are four members of this family in vertebrates, MyoD (also called Myf-3), myogenin (Myf-4), Myf-5 and MRF4 (Myf-6, herculin). A number of recent reviews summarizes in detail the existing knowledge of the structure of the genes, the MyoD-myogenesis model and the activation of muscle tissue-specific genes by the MyoD genes (for reviews see above).

MyoD proteins are expressed specifically in muscle tissue where they act as tissue-specific transcription factors. In vitro they are active after formation of dimer complexes with proteins of the ubiquitously expressed E2A gene. The complex binds to specific transcription regulatory sequences of muscle-specific genes called enhancer regions in the promoters, thereby activating expression of the tissue- and developmental stage-specific genes like muscle-specific actin, tropomyosin and titin (reviewed in Olson, 1990; Weintraub et al., 1991; Lyons and Buckingham, 1992).

Once activated, each member of the MyoD gene family can both positively autoregulate its own expression and regulate the expression of other MyoD genes in differentiating in vitro muscle cell cultures, thereby continuing the differentiation pathway. Thus, once the pathway is activated, myogenesis continues until terminal differentiation is established.

Determinated cells (myoblasts) are able to migrate (step (2) of the myogenesis pathway) and profilerate (step (3)); Olson, 1990, 1992). Irreversible terminal differentiation (step (4)) is induced by fusion of the myoblasts into multinucleated myofibres. The fusion is induced by the activation of the myogenin (Myf-4) gene in myoblasts (Olson, 1990, step (4)).

The research for genetic variation within the MyoD genes is already underway in a number of laboratories. Recently the first polymorphism was reported in the myf-4 gene in pigs (Ernst et al., 1993). Allele freqencies differed between different pig breeds. It is still unclear where in the gene this polymorphism is located and whether this polymorphism could be related to different muscle growth potentials and be used as a marker within selection lines of one breed.

Myogenin is the only myf gene expressed in all skeletal muscle cell lines (Wright et al., 1989; Edmondson and Olson, 1989). Knock out experiments in mice have shown that this protein fulfils an essential function in muscle differentiation by regulating the onset of myoblast fusion and the formation of functional muscle fibers (Hasty et al., 1993; Nabeshima et al., 1993).

RFLPs have been described for the mouse MyoD gene (Kay et al., 1993), the bovine myf-S gene (Dean et al., 1993) and the pig myogenin (Ernst et al, 1993) and myf-6 genes (Ernst et al., 1994). One MyoD allele in mouse seems to be associated with the increased efficiency of muscle regeneration of the SJL/J strain.

DISCLOSURE OF THE INVENTION

Figure 1:
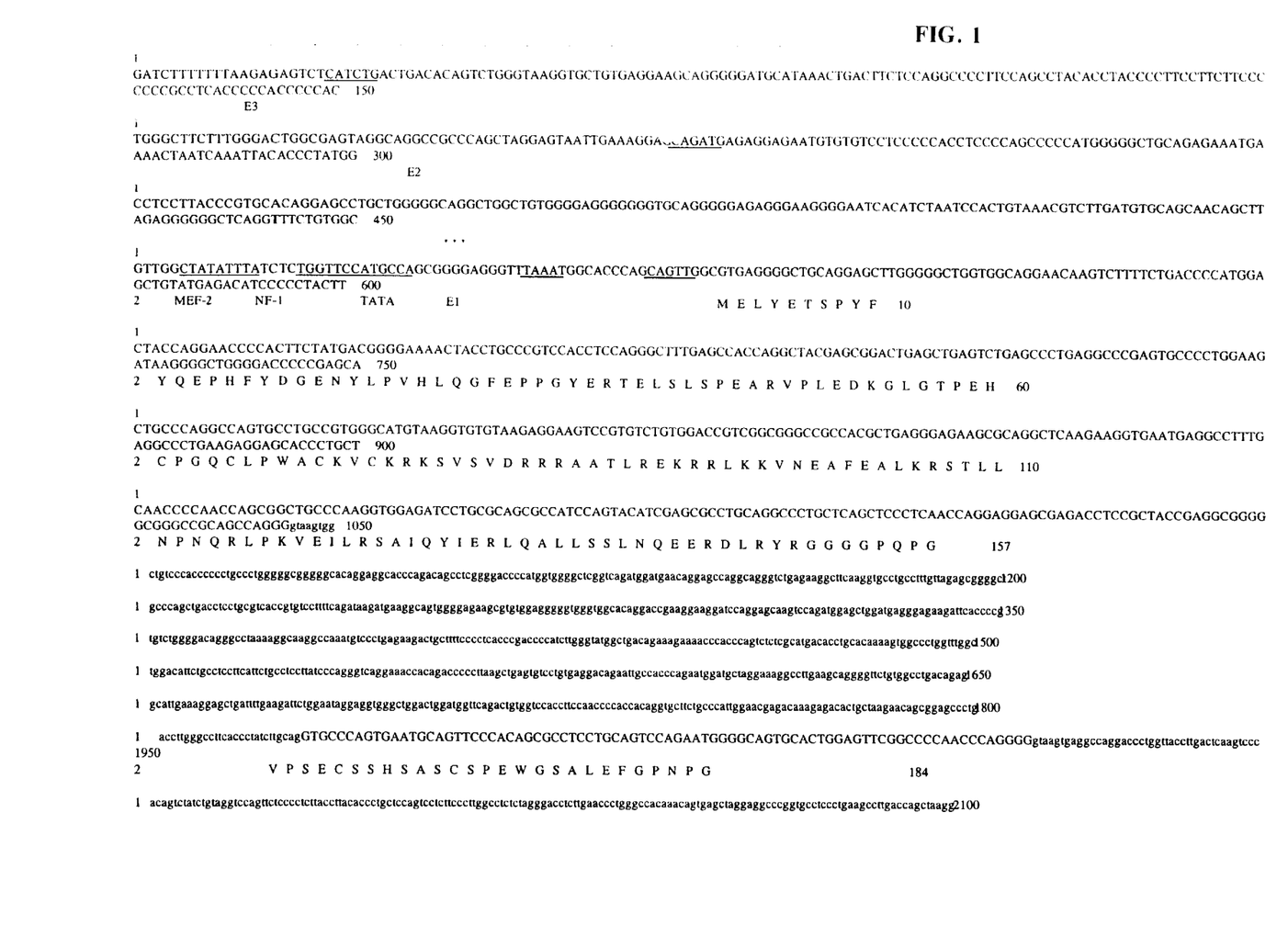
FIG. 1 is a nucleotide sequence of the pig myogenin gene (SEQ ID NO: 9) deduced from the nucleotide sequence (SEQ ID NO: 10)

The present invention provides among others an isolated or recombinant pig myogenin gene specific nucleic acid molecule or pig myogenin gene specific fragments thereof comprising or hybridising to the nucleotide sequence of FIG. 1 (SEQ ID NO 9)or its complementary sequence or the RNA equivalents thereof.

Myogenesis could be an important determinant of the number of muscle fibers present at birth and thus influence production traits such as birth weight or quantitative lean meat production, or other traits of interest. With the present invention, the genetic variation within the myogenin genes in breeding populations can now be revealed and analysed for association of the effects of each of the alleles with production traits of interest. Genetic variation within the myogenin gene could also be associated with different regulation of expression. Since myogenin regulates the moment in time at which differentiation proceeds with fusion of existing myoblasts and the end of myoblast proliferation, delayed or changed expression levels can influence the number of muscle cells formed. With the present invention, the genetic variation within the myogenin genes with respect to variation in regulation of expression can now be revealed and analysed for association with production traits.

The present invention further provides a method to generate via recombinant DNA techniques an animal, such as small laboratory animals or farm animals, i.e. a pig, with additional genetic material originating from the pig myogenin gene. Such animals may than encode wanted alleles of the pig myogenin gene and constitutively or transiently express allelic proteins or fragments thereof that enhance the production characteristics of those animals.

The invention further provides methods to generate proteins or (poly)peptides comprising various allelic proteins or fragments thereof derived from the pig myogenin gene. Such peptides, or antibodies specifically directed against such peptides, may be used to influence production traits in the live animal, but may also be used in cell-culture systems in vitro. Such peptides, or antibodies specifically directed against such peptides, may also be used in diagnostic test systems to select animals that express wanted forms of allelic proteins or fragments thereof encoded by the pig myogenin gene.

The invention further provides methods localising, identifying or marking genes or alleles or quantitative trait loci, in particular of the pig myogenin gene, in samples, in particular biological samples, cells or tissues, such as but not limited to hair, skin or blood, of pigs, by allowing for specific amplification of genomic fragments of those genes or alleles or quantitative trait loci of pigs. Since marker assisted selection of pigs is frequentially based upon genetic variation that exists within functional genes that influence a production trait directly, i.e. genes such as the pig myogenin gene that controls myogenesis, one of the methods that the invention provides is a method that identifies or marks such genes and that can distinguish between characteristics of alleles of those genes which characteristics serve as markers in selection programmes for animals with specific versions of those genes that are directly linked with improved production traits.

The invention further provides a method wherein polymorphic restriction sites within functional genes and thus different alleles of those genes are identified by allowing for specific amplification of genomic fragments of those genes, in particular by allowing for specific amplification of fragments of the myogenin gene. Amplification methods are well known in the art, the best known being PCR. A short description of the PCR used herein is given in the experimental part. Other primers, enzymes and conditions can of course be applied. After amplification a suitable method of identifying wanted alleles is a restriction endonuclease treatment. A suitable restriction enzyme for pig myogenin alleles is MspI but others may also be used. By these methods large numbers of pigs can be rapidly genotyped for studies in which genotypic variation can be associated with growth characteristics and other production traits of pigs However, there are many other methods identifying polymorphisms in alleles, both at the nucleic (DNA/RNA) level and at the product (protein) level. In particular at the protein level there are many possibilities using immunoassays, whereas at he nucleic acid levels there are many assays which all include some kind of hybridisation step of for instance primers or labelled nuclei acids. A very good possibility would be mismatch PCR. Primers to be used in the invention can be identified by the person skilled in the art, the sets given in the experimental part are for illustrative purposes only.

Furthermore, the methods according to the invention can be developed into diagnostic assays or kits by which selection of pigs with alleles of interest can be performed in routine screening protocols employed in breeding programmes. With such protocols better results of selection can be expected when genes responsible for regulation of commercially interesting body tissues can be rapidly identified and controlled.

EXPERIMENTAL

BEST MODE OF THE INVENTION (a) Amplification, cloning and sequence analysis of the porcine myogenin gene.

In order to study genetic variation at the porcine myogenin gene locus, specific PCRs were developed (PCR 1 and 2, Table I). Primers were based on an alignment of human (Salminen et al., 1991) and mouse myogenin sequences (Edmondson et al., 1992). Fragments of 2099 and 442 bp respectively, covering the complete coding sequences and two introns, were obtained by PCR amplification on pig genomic DNA. These fragments were cloned in pUC18 and sequenced (FIG. 1). Like the human and mouse genes, the pig myogenin gene has three exons. The first exon encodes the bHLH domains, which in men, mice and pigs have identical amino acid sequences. Exon 2 encodes 27 amino acids of the transactivation domain (Schwarz et al., 1992) and exon 3 the conserved C-terminal segment, common to the four Myf proteins (Fujisawa-Sehara et al., 1990). The amino acid sequence of pig myogenin is for 97% and 96% identical to the sequence of human and mouse Myogenin, respectively. The first pig intron is 785 bp long and is larger than the corresponding introns of mice and men. The second intron of 639 bp is larger than the mouse but smaller than the human second intron.

The myogenin promoter and 3' non coding sequences were isolated by screening of a porcine genomic library with a mixture of human myf cDNA fragments. Positive phages were purified and myogenin clones were selected by means of PCR 1 and PCR 3 (Table I). The SacI-fragments of two clones (A16, A17) were subcloned in pBS- and sequenced. This revealed 571 bp of the promoter sequences and 856 bp of the 3' untranslated region, containing a putative polyadenylation signal (AATAAA) at positions 3397 to 3402.

Analysis of the pig myogenin promoter for the presence of transcription factor binding consensus sequences revealed three E-box sequences (CANNTG) located at positions 508 to 513 (E1), 210 to 215 (E2) and 22 to 27 (E1). A myocyte-specific enhancer factor 2 (MEF-2) site (456 to 464), a nuclear factor 1 (NF-1) site (469 to 481) and a TATA-box sequence (494 to 498) were identified within 70 bp of the putative transcription start sites. Comparison of the pig sequence with the human and mouse sequences revealed more than 96% sequence identity within the proximal 160 bp upstream from the transcription start sites. This high conservation may be explained by the observation that this region specifies the correct spatial and temporal activation of the mouse myogenin gene during embryological development (Cheng et al., 1993; Yee and Rigby, 1993).

The E1-box is present in the myogenin genes of men, mice and pigs, whereas the E2 box is only conserved between the human and porcine genes. The E1-box has been demonstrated to be the only myogenin binding E-box sequence in the mouse promoter (Edmondson et al., 1992). Funk and Wright (1992) identified MEF-2 and NF-1 as stabilizing factors for the in vitro binding of myogenin to E-box sequences. The presence of binding sites for both factors in the highly conserved minimal proximal promoter sequences of the different myogenin genes indicates that these factors are involved in the regulation of the myogenin expression. Especially the presence of the MEF-2 site appears to be crucial for the correct embryological myogenin expression (Cheng et al., 1993; Yee and Rigby, 1993).

(b) Characterization of a CA-repeat at the myogenin gene locus

A CA-repeat sequence of variable length (19 and 22 repeats) has been identified by Edmondson et al. (1992) and Yee and Rigby (1993) between positions −603 and −560 in the mouse myogenin promoter. (CA)n-repeats, with n>6, are the most abundant highly polymorphic dinucleotide repeats, present in mammalian genomes (Wintero et al., 1992) and they are extensively used as markers in association studies. Because of our interest in polymorphisms closely linked to the myf genes, we also examined the myogenin phage inserts with a (CA)25-repeat probe. This revealed the presence of a CA-repeat sequence at about 5 kb downstream of the TGA termination codon. Sequence analysis of this region demonstrated that the CA-repeat was interrupted by CCC stretches (sequence submitted to the EMBL/GenBank/ DDBJ databases and available under accession number X89210). Since imperfect CA-repeats are generally not polymorphic (Wintero et al., 1992), we did not further examine this region.

(c) Characterization of a polymorphic MspI site at the 3' side of the porcine myogenin gene The presence of a variable 4.2/4.9 kb MspI fragment at the myogenin gene locus has been previously described for different pig breeds by Ernst et al. (1993). Southern blot analysis of 105 unrelated pigs from 7 pig breeds with a probe specific to the 3' side of the myogenin gene (FIG. 2a), and restriction mapping of myogenin subclones, enabled us to localize the described polymorphic Mspl site at the 3' side of the gene and to sequence its flanking regions (sequence submitted to the EMBL/GenBank/DDBJ databases and available under accession number X89209). A PCR-RFLP test (PCR 4, Table 1) for detection of this polymorphic site was developed and used for genotyping the pigs of the panel (FIG. 2b).

All typed breeds except the Meishan, are polymorphic at the detected MspI site (Table II, columns 9, 10, 11). Comparison of the allele frequencies for the different pig breeds tested, shows that the Meishan population under investigation does not contain the 4.2 kb allele. Ernst et al. (1993) also found the 4.9 kb to be the predominant myogenin allele in Chinese pig breeds (Fengjing, Meishan, Minzu). However, this might be explained by the very small numbers (<10) of founder animals of these Chinese pig populations in the US and in Europe (Brascamp, pers. comm.), as well as by the small numbers of animals tested. In Western breeds, the 4.2 kb allele seems to be more frequent, but the allelic distributions depend on breed and population. We found the 4.2 kb allele to be predominant in Duroc and Wild Pig breeds. Both alleles were equally present in Pietrain, Dutch Landrace (DL) and Hampshire, while the Great Yorkshire (GY) population tested was characterized by a high frequency of the 4.9 kb allele.

Figure 3:
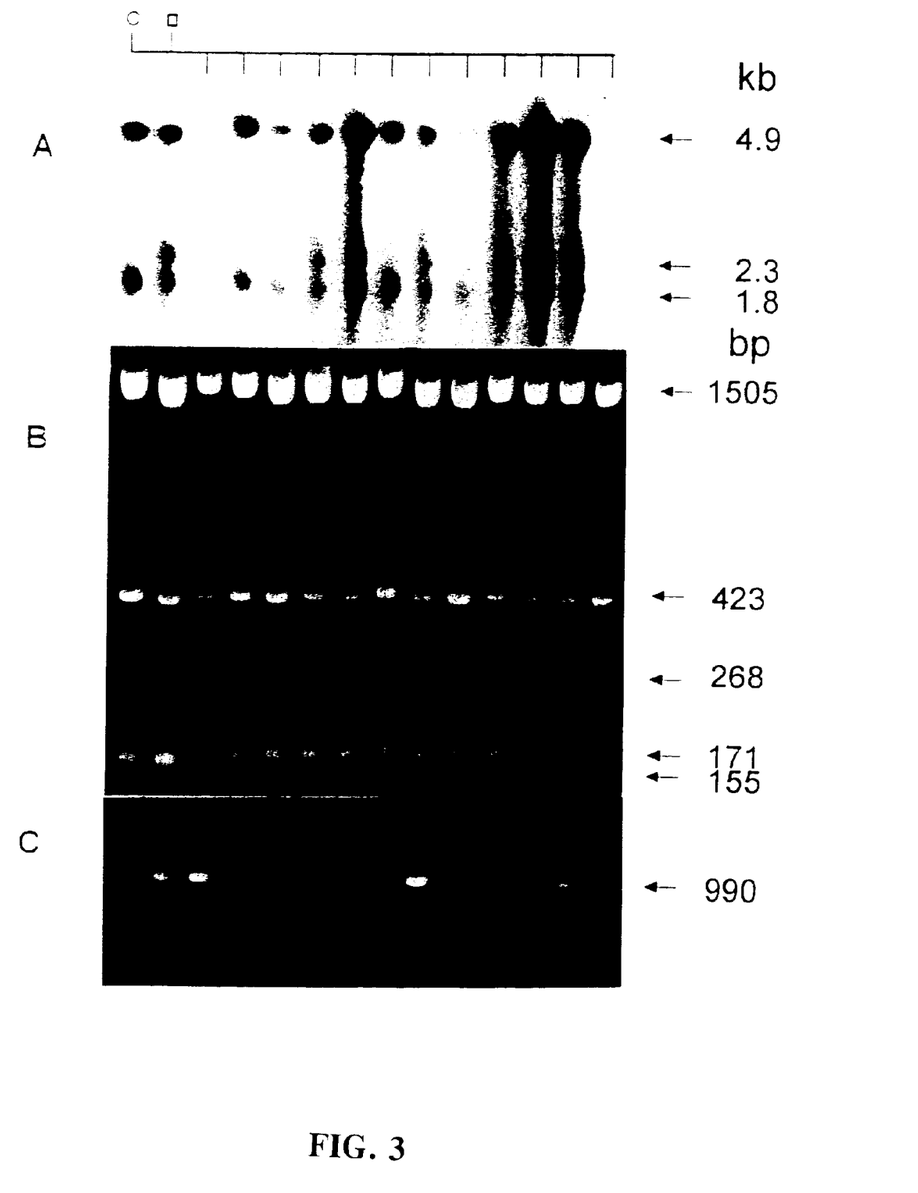
FIG. 3 depicts Mendelian segregation of two MspI polymorphisms at the pig myogenin locus in a two generation family of Meishan pigs, wherein the squares represent sires and the circles represent dam, by: (A) Southern blot analyses of MspI digested gemonic DNA; (B) PCR 1/MspI analysis; and (C) PCR 5 analyses.

(d) Detection and characterization of two additional polymorphic MspI sites at the porcine myogenin gene locus MspI digestion of PCR1 products of the 105 unrelated pigs revealed sequence variation at position 2394 in the second intron. Analysis of the PCR1-MspI patterns shows sequence variation near position 2394 for the Meishan, DL and Duroc breeds (Table II, columns 6, 7, 8). In the Meishan population only, the absence of the 2394 MspI site is coupled to the presence of a 1.8 kb MspI fragment on Southern blot hybridized to the PCR1 probe (FIGS. 3a and b), while in all other breeds only a 2.3 kb MspI fragment is visualized. This implies that in Meishans a third variable MspI site is present in the promoter region of the myogenin gene. Remarkably, several attempts to amplify the concerned region with different primer combinations (e.g. PCR5, Table I) failed to generate a fragment for the Meishan specific allele (FIG. 3c). This suggests that additional sequence variation at the primer hybridization sites hinders proper amplification of the 1.8 kb allele or that a deletion rather than an additional MspI site causes the 1.8/2.3 kb polymorphism.

Figure 4:
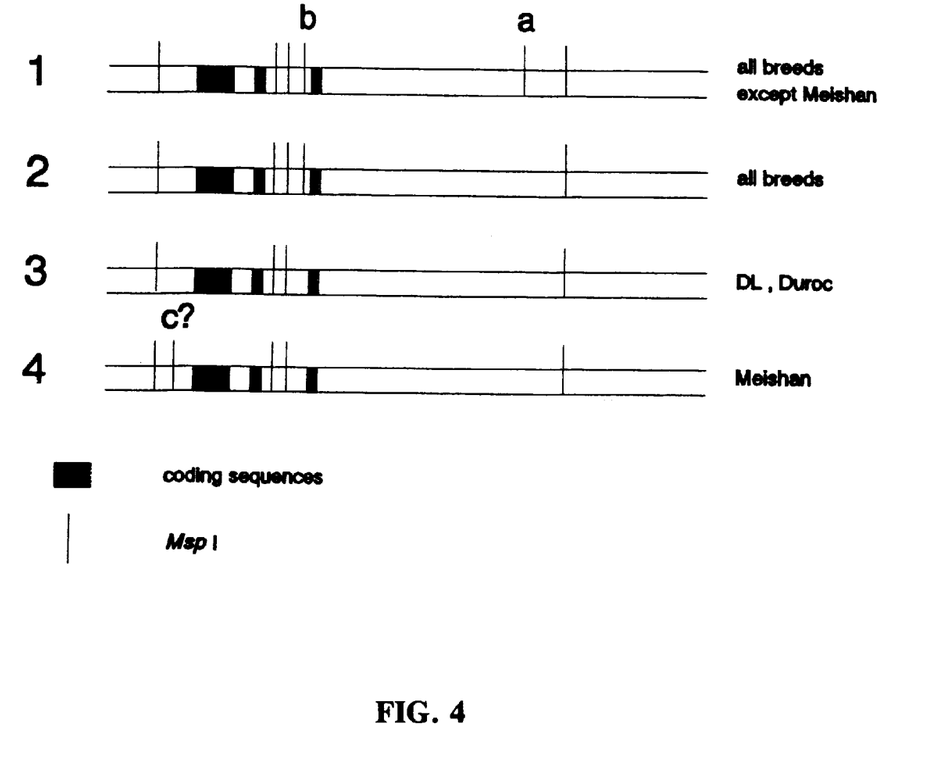
FIG. 4 is a schematic representation of the four myogenin alleles that were distinguished in the tested pig breeds and crosses, based on the different observed combinations of three polymorphic MspI sites, indicated by a, b, and c, at this gene locus.

Autosomal Mendelian segregation of the 1.8 kb and 2.3 kb pig myogenin fragments and of the MspI polymorphism in the second intron was checked in 58 Meishan pigs from 4 two-generation families and in a DL heterozygous x homozygous cross (9 animals, data not shown). Analysis of the genotypes of the 105 unrelated pigs from 7 different breeds, and of the progeny of the DL cross, suggests the presence of at least 4 different myogenin alleles in pigs (FIG. 4). The allele frequencies are breed dependent, with allele 4 being specific for the Meishan breed, allele 3 being only detected in a few animals of the DL and Duroc breeds and alleles 1 and 2 being the predominant alleles in the Western breeds. Large numbers of commercial European pigs will be genotyped in the near future by use of the PCR-RFLP tests for MspI sites a and b (FIG. 4), and the resulting myogenin genotypes will be tested for association with growth characteristics.

(e) Chromosomal assignment of the porcine myogenin gene

Localization of the myogenin gene in the pig genome offers the possibility to use a limited set of microsatellite markers in association studies with growth characteristics. We analysed a panel of 21 pig/rodent somatic cell hybrids for the presence or absence of the pig myogenin gene by myogenin specific PCR 3 amplification (Table I) on genomic DNA. A pig myogenin fragment with a predicted size of 873 bp was amplified, together with the hamster or mouse fragment from the parental rodent cell line, of 650 and 600 bp respectively. The porcine PCR 3 fragment was further identified by EcoRI and PvuII digestion, generating fragments of respectively 313+560 bp and 219+654 bp.

The distribution pattern of specific signals in all hybrids was compared with the signals for all reference loci. The highest concordance for myogenin was 90% and the significant correlation value o was 0.81 for chromosome 9, indicating that myogenin maps to chromosome 9 (Table III). Myogenin has already been mapped by RFLP analysis to chromosome 9 (Archibald et al., 1995). We have confirmed these results by physical mapping with somatic cell hybrids. In human myogenin maps to chromosome lq31-q41. Our result confirms a segment of conserved synteny between human chromosome 1 and porcine chromosome 9, which has been demonstrated by linkage mapping of CR2 (Johansson et al., 1994) and Zoo-FISH analysis (Rettenberger et al., 1995a). Indirectly by these Zoo-FISH data, a localization of myogenin can be predicted to porcine chromosome 9q21-qter, which allows preferential selection of polymorphic markers from this respective region.

(f) Association between myogenin genotypes and growth characteristics.

In a first study to determine association between myogenin genotypes and growth characteristics of pigs originating from populations representing two selection lines of Cofok and Nieuw-Dalland, respectively, the effect of the 3' MspI polymorpic site (denoted as "a") on birth weight was determined. The two selection lines differ considerably, the Cofok line has traditionally been selected on homogeneous weights of all piglets in a litter at birth, whereas the Nieuw-Dalland line has not been selected on this trait. For Cofok, 267, and for Nieuw-Dalland, 147 pigs have been typed separately for site a. The number of Cofok animals in the pedigree file was 23092 while of 14687 of those animals the birth weight was known; the number of Nieuw-Dalland animals in the pedigree file with known birth weight was 22569. Typed animals have a chance of 1 for one specific genotype, and thus a chance of 0 for the remaining 2 genotypes. The genotype frequencies of the typed animals were for AA, Aa, and aa 36%, 46% and 18%, respectively, for the Cofok pigs, and 5%, 38%, and 57% for the Nieuw-Dalland pigs. Frequencies for allele A and a were 0.6 and 0.4, respectively, for the Cofok-data, and 0.24 and 0.76 for the Nieuw-Dalland data. For the animals that were not typed, the respective chances for the three genotypes are in between 0 and 1. These chances have been determined with the algorithme developed by Van Arendonk and others (1987) using the allele frequencies, pedigree data and the data from the typed pigs.

The effects of the three genotypes on birth weight were corrected for among others gender, parity of the sow and litter size. Degrees of heretability ($h^2$) and common environmental components ($c^2$) were estimated once and incorporated in the model. For birth weight $h^2$ and $c^2$ were 0.29 and 0.30, respectively, for the Cofok data; and 0.09 and 0.23, respectively, for the Nieuw-Dalland data.

For the Cofok data, the estimated effects of the genotypes AA or Aa on birth weight were 13.04 g (standard error (SE) 38.79) versus −47.61 g (SE 36.68) (the effects of aa were set on 0 g), for the Nieuw-Dalland data the effects of AA or Aa were 117.89 g (SE 177.20) versus −30.60 g (SE 75.36).

The estimated contrast of birth weights associated with genotype AA or Aa of the Cofok pigs was significantly different from 0 (60.65 g; SE 27.29); with the Nieuw-Dalland pigs the difference between AA and Aa pigs was 148.49 g (SE 224.25), however, this large difference was not found to be significant, possibly due to the small number of AA pigs typed and the large SE found.

In a second study the effect of the 3' MspI polymorpic site (denoted as "a") on birth weight was determined. The two selection lines differ considerably, the Cofok line has traditionally been selected on homogeneous weights of all piglets in a litter at birth, whereas the Nieuw-Dalland line has not been selected on this trait. For Cofok, 606, and for Nieuw-Dalland, 1043 pigs have been typed separately for site a. The number of Cofok animals in the pedigree file was 19148 while of 14295 of those animals a record with fenotypic data was known; the number of Nieuw-Dalland animals in the pedigree file with known fenotypic data was 13244. Typed animals have a chance of 1 for one specific genotype, and thus a chance of 0 for the remaining 2 genotypes. The genotype frequencies of the typed animals were for AA, Aa, and aa 23%, 43% and 34%, respectively, for the Cofok pigs, and 16%, 46%, and 38% for the Nieuw-Dalland pigs. Frequencies for allele A and a were 0.45 and 0,55, respectively, for the Cofok-data, and 0.39 and 0.6 for the Nieuw-Dalland data. For the animals that were not typed, the respective chances for the three genotypes are in between 0 and 1. These chances have been determined with the algorithme developed by Van Arendonk and others (1987) using the allele frequencies, pedigree data and the data from the typed pigs.

The effects of the three genotypes on birth weight were corrected for among others gender, parity of the sow and litter size. Degrees of heretability ($h^2$) and common environmental components ($c^2$) were estimated once and incorporated in the model. For birth weight $h^2$ and $c^2$ were 0.22 and 0.327, respectively, for the Cofok data; and 0.27 and 0.20, respectively, for the Nieuw-Dalland data.

The estimated contrast of birth weights associated with genotype AA or Aa of the Cofok pigs was significantly different from 0 (69.7 g; SE 24.5); with the Nieuw-Dalland pigs the difference between AA and Aa pigs was 40.7 g (SE 30.1), however, this large difference was not found to be significant, possibly due to the small number of AA pigs typed and the large SE found. The two independent studies above showed comparable results.

In a third study, it was shown that MyoD-genes influence the onset of muscle development, the meat percentage of offspring is associated with the myf4-polymorphism of their sire.

Boars from a specialized boarline (line OBO) of the DALLAND breeding programme are routinely used in a commercial herd to produce offspring. Each piglet is identified at birth and followed until it is slaughtered. In total 2303 animals, gilts and boars, were slaughtered during 4 years.

Meat percentage is analysed using the following model:

$$Y = \mu + BV\_BF + MG\_BF + b^*S/W + Period + Geno + Sire(Geno) + e$$

where

Y=Meatpercentage determined by HGP, official Dutch classification

BV_BF=EBV of the sire for backfat

MG_BF=probability of the major gene for backfat being AA of the sire

SIW=linear regression of slaughterweight on meat percentage

Period=date of slaughter, 8 period of 6 months

Geno=Genotype of the sire with respect to Myf4 (AA, Aa, aa)

Sire(Geno)=effect of sire nested within genotype e=residual error (variation between animals within sires)

HGP formule combines a measure of backfat and a measure of loin depth, therefore the model contains estimates of backfat, to get a better estimate of the real muscle percentage. Slaughterweight is known to have a significant effect on meatpercentage.

Sequential sums of squares are calculated for effects in the order as given in the model, using SAS GLM procedure (Type I SS). To test the effect of Myf4-genotype on meatpercentage the variation between genotypes is tested against variation within genotype, i.e. among sires.

Results

All effects in the model were highly significant (p<0.001). The test of Geno versus Sire(geno) was also significant, p<0.0268. The estimated effect of the Myf4 alleles were:

| Genotype | meatpercentage (HGP) |
|----------|---------------------|
| aa       | 56.74               |
| Aa       | 56.36               |
| AA       | 57.26               |

In addition, for growth parameters no significant effect was found, probably due to the limited amount of data. However, there was a tendency for the heterozygote to be superior.

Given the results mentioned in the third study one can design a breeding programme with specialized lines with e.g. a high or low meat %.

Conclusions (1) PCR amplification on porcine genomic DNA and screening of a genomic library with human myf cDNA fragments has enabled the isolation and characterization of the pig myogenin gene.

(2) Sequence analysis of a 3.5 kb fragment revealed high similarity in coding and proximal promoter regions between pig, human and mouse myogenin genes.

(3) Three polymorphic MspI sites were found in the promoter region, in the second intron and at the 3' side of the gene, respectively. In a panel of 105 unrelated pigs and in several Meishan families, at least 4 myogenin alleles were identified, some of which were breed specific. PCR tests for the rapid identification of these alleles were developed. This allows association studies with the growth performances of pigs.

(4) Myogenin was assigned to pig chromosome 9.

(5) A statistically significant association has been found between alleles of the 3' MspI polymorphic site (site a) and effects on birth weight in a selection line of pigs.

TABLE I

Primer sequences, annealing temperatures and fragment characteristics for PCR amplification reactions of different regions of the pig myogenin gene.

| AMPLIFIED REGION (NUCLEOTIDE NRS) | PRIMER (SEQUENCES | ANNEALING TEMPERATURE | PREDICTED SIZE OF AMPLIFIED PRODUCT |
|---|---|---|---|
| PCR 1[a] Coding regions and introns 572 2654 | FW:M4 5'-GGAATTCCATGGAGCTGTATGARACATC (SEQ ID NO•1) REV:M4R 5'-GGAATTCCAATCTCAGTTGGGCATGGT (SEQ ID NO•2) | 61° C. | 2099 bp |
| PCR 2[a] EXON 1 572-1005 | FW:M4 5'-GGAATTCCATGGAGCTGTATGARACATC (SEQ ID NO•1) REV: M4Rp 5'-TCRCGCTCCTCCTGGTTGA (SEQ ID NO•3) | 61° C. | 442 bp |
| PCR 3[a] EXON 1-EXON2 988-1858 | FW:MMYOGi 5'-CAACCAGGAGGAGCGCGATCTCCG* (SEQ ID NO•4) REV:MMYOGc 5'-AGGCGCTGTGGGAGTTGCATTCACT* (SEQ ID NO•5) | 59° C.–61° C. | 871 bp |
| PCR 4[a] 3'-SIDE | FW:M4P2 5'-TCAGGAAGAACTGAAGGCTG (SEQ ID NO•6) REV:IP12 5'-GTTTCCTGGGGTGTTGC (SEQ ID NO•7) | 60° C. | 353 bp |
| PCR 5[a] 5'-SIDE 16-1005 | FW:M4P3 5'-GAGTCTCATCTGACTGACAC (SEQ ID NO•8) REV:M4Rp 5'-TCRCGCTCCTCCTGGTTGA (SEQ ID NO•3) | 60° C. | 990 bp |

Nucleotide numbers are according to the pig genomia sequence in FIG. 1;
fw: forward primer;
rev: reverse primer;
*: primer sequences, previously described by Montarras et al., 1991.

[a] PCR amplifications were performed on genomic DNA and on phage DNA. Genomic DNA was isolated as described (Sambrook et al., 1989) from EDTA-treated blood samples stored at −80° C. Phage DNA was purified from isolated phage clones by the plate lysate method (Sambrook et al, 1989). Myogenin specific PCR amplifications were performed on 50 ng genomic DNA or on 1 μl of 1:1000 dilutions of phage DNA preparations in 50 μl containing 1.25 U Taq DNA polymerase (Perkin Elmer Cetus, Norwalk, Conn.) or 0.2 U Super Tth polymerase (SphaeroQ, Leiden, The Netherlands) in the appropriate buffer, 20 pmole of forward and reverse primer, and 0.2 mM of each dNTP (Boehringer Mannheim, Germany). After 5 min of denaturation at 95° C., 35 cycles were carried out of 1 min denaturation at 95° C., 1 to 2 min annealing at the indicated temperature and, depending on the length of the target sequence, 1, 2 or 4 min of elongation at 72° C.

Legend to the Figures

FIG. 1: Structure and nucleotide sequence of the pig myogenin gene.

Myogenin gene fragments were isolated by PCR amplification on genomic DNA (PCR 1 and PCR 2, Table 1) or by screening of a genomic library with human myf cDNAs. SacI fragments isolated from two myogenin containing phage clones (A16 and 17) were subcloned in pBS- and sequenced. Sequence data of the indicated segments were submitted to the EMBL data base and are available under accession numbers X89007, X89209, X89210. Nucleotide sequence (SEQ ID NO: 9) and deduced amino acid sequence (SEQ ID NO: 10) of the pig myogenin gene. Intron sequences are shown in lower case letters; putative TATA box, polyadenylation signal, E-boxes and other regulatory sequences are underlined; arrows denote putative transcription start sites, analogous to human and mouse genomic sequences (Salminen et al., 1991; Edmondson et al, 1992; Yee and Rigby, 1993).

Methods: The sequence was obtained by dideoxy sequencing (Sanger et al., 1977) of (1) PCR fragments amplified on genomic DNA by PCR 1 and 2 (Table 1) and cloned in pUC18, and (2) by analysis of myogenin SacI fragments isolated from a genomic library. These fragments were obtained by screening 0.5×106 plaque forming Units (pfU) of a porcine genomic library in the phage vector EMBL3/SP6/T7 (Clontech Laboratories Inc. Palo Alto, Calif.) by hybridization to the four radioactively labelled human myf cDNA fragments (purchased from ATCC, Rockville, Md.; Braun et al. 1989a, 1989b, 1990). After hybridization on duplicate filter lifts (nitrocellulose) for 16 h at 68° C. in 6×SSC, 0.5% (w/v) SDS, 10 mM EDTA, 5×Denhardt's solution, 100 μg salmon sperm DNA per ml, filters were washed three times for 10 min in 6×SSC, 0.1% (w/v) SDS and once for 30 min in 2×SSC, 0.1% (w/v) SDS at room temperature. Thirty seven clones remained positive after three successive rounds of plaque purification. Phage DNA was purified by the plate lysate method (Sambrook et al, 1989) and 17 myogenin positive clones were identified by PCR 1 and PCR 3 amplification (Table 1) on purified phage DNA. Inserts were analysed by XlloI and SacI digestion and Southern (1975) blot hybridization with the myf cDNA probes. SacI fragments of 2 representative clones were subcloned in pBS- and sequenced.

Figure 2:
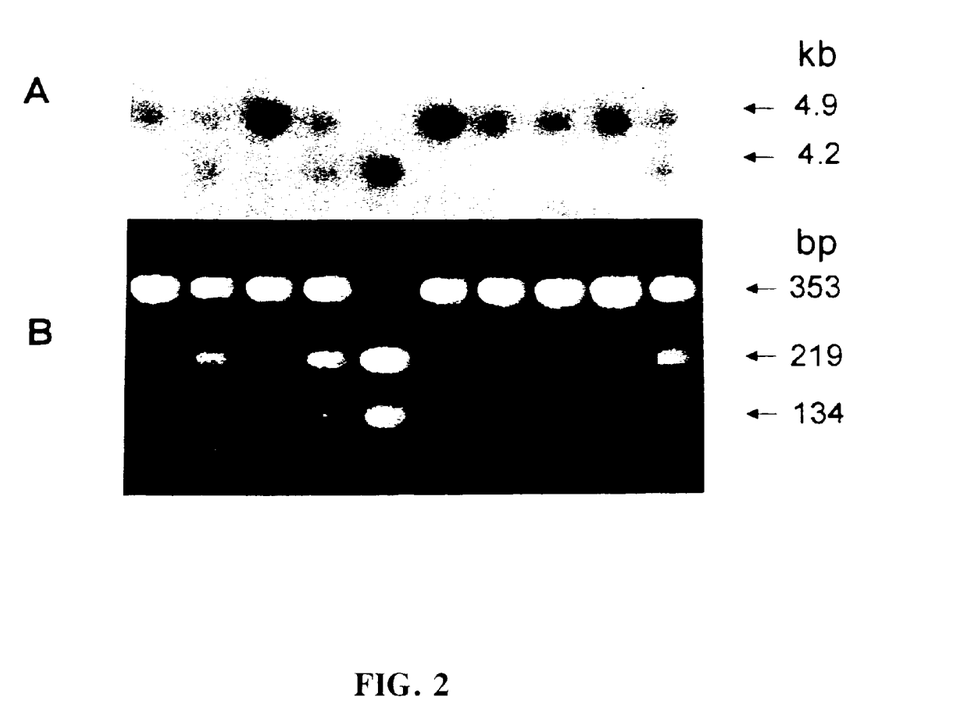
FIG. 2A depicts a polymorphic MspI site at the 3' side of the myogenin gene as detected by Southern RFLP analysis of the digested genomic DNA of Great Yorkshire boars, the Southern RFLP analysis reveals a polymorphic fragment (4.2/4.9 kb)
FIG. 2B depicts a polymorphic MspI site at the 3' side of the myogenin gene as detected by PCR-RFLP analysis of the DNA of Great Yorkshire boars; a fragment of 353 bp is amplified and digested with MspI, resulting in the 353 bp fragment that corresponds to the 4.9 kb fragment in FIG. 2A, or in 134 and 219 bp fragments that correspond to the 4.2 kb fragment in FIG. 2A.

FIG. 2: Detection of a polymorphic MspI site at the 3' side of the myogenin gene by Southern RFLP and PCR-RFLP analysis. A. Southern blot analysis of MspI digested genomic DNA of 8 Great Yorkshire (GY) boars, hybridized to a 3' specific myogenin probe, revealing a polymorphic fragment (4.2/4.9 kb) as described by Ernst et al. (1993). B. PCR 4-MspI analysis of 8 GY boars. A fragment of 353 bp is amplified (Table 1) and digested with MspI, resulting in the 353 bp fragment, corresponding to the 4.9 kb fragment in A, or in 134 bp and 219 bp fragments, corresponding to the 4.2 kb fragment in A.

Methods: Ten μg of porcine genomic DNA, isolated from EDTA treated blood as described (Sambrook et al., 1989), was digested with 100 U MspI (Boehringer) following the manufacturer's instructions, for 16 h at 37° C. After precipitation, digested DNA was electrophoresed in a 0.8% (w/v) agarose gel (Sigma, St Louis, Mo.) and transferred to positively charged nylon membranes (Boehringer Mannheim) by Southern blotting (Southern, 1975). After fixation of the DNA (30 min, 120° C.), membranes were hybridized in a solution containing 5×SSC, 1% (w/v) blocking solution (Boehringer), 0.1% lauroyl-sarcosine, 0.02% (w/v) SDS, for 16 h at 680° C. Membranes were washed at room temperature three times for 2 min in 2×SSC, 0.1% (w/v) SDS and twice for 30 min in 0.1×SSC, 0.1% (w/v) SDS. Hybridizing fragments were visualized by autoradiography at −80° C. for 2 days to 1 week.

TABLE II

Frequency of myogenin genotypes in 7 pig breeds, based on three polymorphic MspI sites.

| BREED | NR[b] | PROMOTER[c] | | | INTRON 2[d] | | | 3'END[c,e] | | |
|---|---|---|---|---|---|---|---|---|---|---|
| | | 1.8/1.8 | 1.8/2.3 | 2.3/2.3 | 2/2 | 2/3 | 2/3 | 4.2/4.2 | 4.2/4.9 | 4.9/4.9 |
| MEISHAN | 11 | 9% | 36% | 55% | 9 | 36% | 55% | 0% | 0% | 100% |
| PIETRAIN | 5 | 0% | 0% | 100% | 0% | 0% | 100% | 40% | 20% | 40% |
| DUROC | 10 | 0% | 0% | 100% | 0% | 10% | 90% | 50% | 50% | 0% |
| WILD PIG | 10 | 0% | 0% | 100% | 0% | 0% | 100% | 60% | 40% | 0% |
| GY[a] | 40 | 0% | 0% | 100% | 0% | 0% | 100% | 2.5% | 20% | 77.5% |
| DL[a] | 20 | 0% | 0% | 100% | 0% | 10% | 90% | 30% | 40% | 30% |
| HAMPSHIRE | 9 | 0% | 0% | 100% | 0% | 0% | 100% | 22% | 56% | 22% |

[a] GY: Great Yorkshire; DL: Dutch Landrace b number of unrelated pigs tested c Pigs were genotyped by Southern RFLP analysis. The myogenin PCR 1 probe, comprising the complete coding sequences and introns, detects a 2.3 kb/1.8 kb MspI polymorphism in Meishan pigs. DNA treatment and hybridization conditions are as described in FIG. 2. d Pigs were genotyped by PCR 1/MspI RFLP analysis, detecting an MspI polymorphism in the second intron at position 2394; 2 denotes the absence, 3 the presence of the MspI site at position 2394. Pigs were genotyped by (1) Southern RFLP analysis with a 3' specific probe, comprising 195 bp of intron 2 and exon 3 and 4 kb of 3' untranslated sequences, hybridizing to polymorphic 4.2 kb/4.9 kb MspI restriction fragments, and (2) PCR 41MspI RFLP analysis, visualizing the same MspIpolymorphism at the 3' side of the gene. Experimental conditions were as described in Table I and FIG. 2.

FIG. 3: Mendelian segregation of two MspI polymorphisms at the pig myogenin gene locus in a two generation family of Meishan pigs (square denotes sire, circle denotes dam).
A. Southern blot analysis of MspI digested genomic DNA, hybridized to the myogenin PCR 1 fragment (Table I, FIG. 1), visualizing 2.3/1.8 kb polymorphic MspI fragments. Square denotes sire; circle denotes dam. DNA treatments and hybridization conditions are as described in FIG. 2.
B. PCR 1/MspI analysis (Table I), detecting an MspI polymorphism in the second intron of the myogenin gene at position 2394; the amplified fragment of 2099 bp is digested by MspI, resulting in 4 fragments of 1505, 171, 155 and 268 bp or in 3 fragments of 1505, 171 and 423 bp.
C. PCR 5 analysis (Table I), showing the presence of the 2.3 kb allele by amplification of a fragment of 990 bp.

FIG. 4: Schematic representation of the 4 myogenin alleles that were distinguished in the pig breeds and crosses tested, based on the different observed combinations of three polymorphic MspI sites at this gene locus. The polymorphic sites are indicated by a, b, c?.

TABLE III

Statistical analysis for concordance and correlation of myogenin with pig chromosomes

| CHROMOSOME/ REFERENCE LOCI[a] | con[b] | ø[c] |
|---|---|---|
| 1/IFNA | 67 | 0.41 |
| 2/S0091 | 67 | 0.41 |
| 3/APOB | 81 | 0.63 |
| 4/S0001 | 52 | 0.04 |
| 5/S0092 | 67 | 0.36 |
| 6/RYR1 | 62 | 0.35 |
| 7/TNFB | 76 | 0.51 |
| 8/ALB | 71 | 0.37 |
| 9/S0095 | 90 | 0.81 |
| 10/S0038 | 81 | 0.60 |
| 11/S0009 | 52 | 0.04 |
| 12/GH | 81 | 0.59 |
| 13/S0076 | 43 | −0.16 |
| 14/DAO | 48 | 0.01 |
| 15/S0088 | 38 | −0.23 |
| 16/S0006 | 52 | −0.01 |
| 17/ENDO | 62 | 0.28 |
| 18/S0062 | 52 | 0.14 |
| X/S0022 | 46 | −0.08 |
| Y/SRY | 62 | 0.44 |

[a] Establishment and cytogenetic characterization by QFQ-banding and FISH of 21 porcine x rodent somatic cell hybrids as well as analysis by PCR has been described earlier in detail (Rettenberger et al., 1994a, 1994b, 1994c, 1995b). b,c Statistical evaluation for concordance and correlation coëfficient ϕ has been performed according to Chevalet and Corpet (1986). The distribution pattern of myogenin was compared with the distribution pattern of the reference loci in each hybrid. Concordance corresponds to the percentage of hybrids which are identical for the presence/absence of the reference locus and myogenin. A marker is syntenic with a reference locus if the correlation coëfficient ϕ is >0.74 for n=20 hybrid lines, with a probability of 2.5% of making an incorrect decision; if ϕ<0.59, synteny can be excluded. The values for chromosome 9 where myogenin maps to, are typed in bold.

REFERENCES

Archibald, A. L., Haley, C. S., Brown, J. F., et al.: The PiGMaP consortium linkage map of the pig (Ss scrofa). Mamm. Genome 6 (1995)157–175.

Braun, T., Bober, E., Buschhausen-Denker, G., Kotz, S., Grzeschik, K.-H. and Arnold, H. H.: Differential expression of myogenic determination genes in muscle cells: possible autoactivation by the Myf gene products. EMBO J. 8 (1989a) 3617–3625.

Braun, T., Buschhausen-Denker, G., Bober, E., Tannich, E. and Arnold, H. H.: A novel human muscle factor related to but distinct from MyoD1 induces myogenic conversion in 1OT1/2 fibroblasts. EMBO J. 8 (1989b) 701–709.

Braun, T., Bober, E., Winter, B., Rosenthal, N. and Arnold, H. H.: Myf-6, a new member of the human gene family of myogenic determination factors: evidence for a gene cluster on chromosome 12. EMBO J. 9 (1990) 821–831.

Cheng, T.-C., Wallace, M. C., Merlie, J. P. and Olson, E. N.: Separable regulatory elements governing myogenin transcription in mouse embryogenesis. Science 261 (1993) 215–218.

Chevalet C. and Corpet F.: Statistical decision rules concerning synteny or independence between markers. Cytogenet. Cell Genet. 43 (1986)132–139.

Chomczynski, P. and Sacchi, N.: Single-step method of RNA isolation by acid guanidinium thiocyanatephenol-chloroform extraction. Anal. Biochem. 162 (1987) 156–159.

Dean, R. G., Benyshek, L. and Kerr, M.: Restriction fragment length polymorphisms in the bovine myogenic gene bmyf. Anim. Biotech. 4 (1993) 43–46.

edgerton V. R.; Roy, R. R., 1991; Regulation of skeletal muscle fiber size, shape and function. J. Biomechanic, 24; (suppl. 1), 123–133.

Edmondson, D. G. and Olson, E. N.: A gene with homology to the myc similarity region of MyoD1 is expressed during myogenesis and is sufficient to activate the muscle differentiation program. Genes Dev. 3 (1989) 628–640.

Edmondson, D. G., Cheng, T.-C., Cserjesi, P., Chakraborty, T. and Olson, E. N.: Analysis of the myogenin promoter reveals an indirect pathway for positive autoregulation mediated by the musclespecific enhancer factor MEF-2. Mol. Cell. Biol. 12 (1992) 3665–3677.

Ernst, C. W., Vaske, D. A., Larson, R. G. and Rothschild, M. F.: Rapid communication: MspI restriction fragment length polymorphism at the swine myogenin locus. J. Anim. Sci. 71 (1993) 3479.

Ernst, C. W., Vaske, D. A., Larson, R. G., White, M. E. and Rothschild, M. F.: Rapid communication: MspI restriction fragment length polymorphism at the swine MYF6 locus. J. Anim. Sci. 72 (1994) 799.

Fujisawa-Sehara, A., Nabeshima, Y., Hosoda, Y., Obinata, T. and Nabeschima, Y. Myogenin contains two domains conserved among myogenic factors. J. Biol. Chem. 265 (1990) 15219–15223. Funk, W. D.; Ouellette, M.; Wright, W. E., 1991: Molecular biology of myogenic regulatory factors, Mol. Biol. Med. 8: 185–195.

Funk, W. D. and Wright, W. D.: Cyclic amplification and selection of targets for multicomponent complexes: Myogenin interacts with factors recognizing binding sites for basic helix-loop-helix, nuclear factor 1, myocyte-specific enhancer-binding factor 2, and COMP1 factor. Proc. Natl. Acad. Sci USA 89 (1992) 9484–9488.

Gunning, P.; Hardeman, E., 1991: Multiple mechanismes regualte muscle fiber diversity. FASEB J. 5: 3064–3070.
Handel, S. E. and Stickland, N. C.: Muscle cellularity and its relationship with birth weight and growth. J. Anat. 139 (1984) 726.

Handel S. E. and Stickland N. C.: Catch-up growth in pigs: relationship with muscle cellularity. Anim. Prod. 47 (1988) 291–295.

Hanset, R., Micheaux, C., Dessy-Doize, C. and Burtonboy, G.: Studies on the 7th rib cut in doublemuscled and conventional cattle. Anatomical, historical and biochemical aspects. In: King, J. W. B. and Ménissier, F. (Eds), Muscle hypertrophy of genetic origin and its use to improve beef production. Marinus Nijhoff, The Hague, 1982, pp. 341–349.

Hasty, P., Bradley, A., Morris, J. H., Edmondson, D. G., Venuti, J. M., Olson, E. N. and Klein, W. H.: Muscle deficiency and neonatal death in mice with a targeted mutation in the myogenin gene. Nature 364 (1993) 501–506.

Johansson, M., Ellegren, H., Marklund, L., Coppieters, W. and Andersson, L.: Linkage maps of porcine chromosome 3, 6, 9 based on 31 polymorphic markers. Mamm. Genome 5 (1994) 785–790.

Kay, P. H., Marlow, S. A., Mitchell C. A. and Papadimitriou, J. M.: Studies on the evolution and function of different forms of the mouse myogenic gene Myo-DI and upstream flanking region. Gene 124 (1993) 215–222.

Lyons, G. E. and Buckingham, M. E.: Developmental regulation of myogenesis in the mouse. Dev. Biol. 3 (1992) 243–253. Montarras, D., Chelly, J., Bober, E., Arnold, H., Ott, M.-O., Gros, F. and Pinset, C.: Developmental patterns in the expression of myfS, MyoD, myogenin and MRF4 during myogenesis. The new Biologist 3 (1991) 592–600.

Nonaka, I. and Nabeshima, Y. Myogenin gene disruption results in perinatal lethality because of severe muscle defect. Nature 364 (1993) 532–535.

Olson, E. N.: MyoD family: a paradigm for development? Genes Dev. 4 (1990) 1454–1461.

Olson, E. N.; 1992: Interplay between proliferation and differentiation within the myogenic lineage. Develop. Biol. 154: 261–272.

Rettenberger, G., Fries, R., Engel, W., Scheit, K. H., Dolf, G. and Hameister, H.: Establishment of a partially informative porcine somatic cell hybrid panel and assignment of the loci for transition protein 2 (TNP2) and protamine 1 (PRM1) to chromosome 3 and polyubiquitin (UBC) to chromosome 14. Genomics 21 (1994a) 558–566.

Rettenberger, G., Burkhardt, E., Adham, I. M., Engel, W., Fries, R., Klett, C. and Hameister, H.: Assignment of the Leydig-insulin like hormone to porcine chromosome 2q12-q13 by somatic cell hybrid analysis and fluorescence in situ hybridisation. Mamm. Genome 5 (1994b) 307–309.

Rettenberger, G., Fredholm, M. and Fries, R.: Chromosomal assignment of porcine microsatellites by use of a somatic ell hybrid mapping panel. Anim. Genet. 25 (1994c) 343–345.

Rettenberger, G., Klett, C., Zechner, U., Kunz, J., Vogel, W. and Hameister, H.: Visualization of the conservation between pigs and humans by heterologous chromosomal painting. Genomics 26 (199Sa) 372–378.

Rettenberger G., Bruch, J., Beattie, C. W., Moran, C., Fries, R. and Hameister, H.: Chromosomal assignment of 17 porcine microsatellites and genes by use of a somatic ell hybrid mapping panel. Anim. Genet. (1995b), in press.

Rohrer, G. A., Alexander, L. J., Keele, J. W., Smith, T. P. and Beattie, C. W.: A microsatellite linkage map of the porcine genome. Genetics 136 (1994) 231–245.

Salminen, A., Braun, T., Buchberger, A., Jurs, S., Winter, B. and Arnold, H. H.: Transcription of the muscle regulatory gene M4 is regulated by serum components, peptide growth factors and signaling pathways involving G proteins. J. Cell Biol. 115 (1991) 905–917.

Sambrook, J., Fritsch, E. F. and Maniatis, T: Molecular cloning: a laboratory manuel. Cold Spring Harbor Laboratory, Cold Spring Harbor, NY, 1989.

Sanger, F., Nicklen, S. and Coulson, A. R.: DNA sequencing with chain-terminating inhibitors. Proc. Natl Acad. Sci. USA 74 (1977) 5463–5467.

Schwarz, J. J., Chakraborty, T., Martin, J., Zhou, J. and Olson, E. N.: The basic region of myogenin cooperates with two transcription activation domains to induce muscle-specific transcription. Mol. Cell. Biol. 12 (1992) 266–275.

Southern E. M.: Detection of specific sequences among DNA fragments separated by gel electrophoresis J. Mol. Biol. 98 (1975) 503–517.

Swatland, H. J. and Kiefer, N. M.: Fetal development of double muscled condition in cattle. J. Anim. Sci. 38 (1974) 752–757.

Te Pas, M. F. W and Visscher, A. H.: Genetic regulation of meat production by embryonic muscle formation—a review. J. Anim. Breed. Genet. 111 (1994) 404–412.

Weintraub, H., Davis, R., Tapscott, S., Thayer, M., Krause, M., Benezra, R., Blackwell, T. K., Turner, D., Rupp, R., Hollenberg, S., Zhuang, Y. and Lassar, A.: The myoD gene family: nodal point during specification of the muscle cell lineage. Science 251 (1991) 761–766.

Wintero, A. K., Fredholm, M. and Thomson, P. D.: Variable (dG-dT)n.(dC-dA)n sequences in the porcine genome. Genomics 12 (1992) 281–288.

Wright, W. E., Sassoon, D. A. and Lin, V. K.: Myogenin, a factor regulating myogenesis, has a domain homologous to MyoD. Cell 56 (1989) 607–617.

Yee, S.-P. and Rigby, P. W. J.: The regulation of the myogenin gene expression during the embryonic development of the mouse. Genes Dev. 7 (1993) 1277–1289.

What is claimed is:

1. A recombinant nucleic acid molecule comprising sequences from the 3' side of the pig myogenin gene, wherein said nucleic acid molecule is obtained by amplifying pig nucleic acids with a primer pair consisting of SEQ ID NO: 6 and SEQ ID NO: 7.

* * * * *

UNITED STATES PATENT AND TRADEMARK OFFICE
CERTIFICATE OF CORRECTION

PATENT NO. : 6,143,880
DATED : November 7, 2000
INVENTOR(S) : Ann Elisabeth Soumillion and Marinus Frederik te Pas It is certified that error appears in the above-identified patent and that said Letters Patent is hereby corrected as shown below:

Column 4,
Line 3, insert a period after "pigs"
Line 8, change "he" to -- the --.

Column 8,
Line 21, change "fenotypic" to -- phenotypic --
Line 29, change "0,55," to -- 0.55, --

Column 9,
Line 40, Table I, change the heading "PRIMER (SEQUENCES" to -- PRIMER SEQUENCES --

Column 11,
Line 62, change "CDNA" to -- cDNA --

Column 12,
Line 32, after "0.1%" and before "lauroyl-" insert -- (w/v) N- --
Line 33, change "680ºC" to -- 68ºC --

Column 14,
Line 59, change "regualte" to -- regulate --

Column 15,
Line 45, change "ell" to -- cell --

Column 16,
Line 5, change "ell" to -- cell --

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear    (ii) MOLECULE TYPE: other nucleic acid    (iii) HYPOTHETICAL: NO (xi) SEQUENCE DESCRIPTION: SEQ ID NO: 1:

GGAATTCCAT GGAGCTGTAT GARACATC                                              28

(2) INFORMATION FOR SEQ ID NO: 2:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO: 2:

GGAATTCCAA TCTCAGTTGG GCATGGT                                               27

(2) INFORMATION FOR SEQ ID NO: 3:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO: 3:

TCRCGCTCCT CCTGGTTGA                                                        19

(2) INFORMATION FOR SEQ ID NO: 4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO: 4:

CAACCAGGAG GAGCGCGATC TCCG                                                  24

(2) INFORMATION FOR SEQ ID NO: 5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO: 5:

AGGCGCTGTG GGAGTTGCAT TCACT                                                 25

(2) INFORMATION FOR SEQ ID NO: 6:

(i) SEQUENCE CHARACTERISTICS:
            (A) LENGTH: 20 base pairs
            (B) TYPE: nucleic acid (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 6:

TCAGGAAGAA CTGAAGGCTG                                                      20

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 7:

GTTTCCTGGG GTGTTGC                                                         17

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 8:

GAGTCTCATC TGACTGACAC                                                      20

(2) INFORMATION FOR SEQ ID NO: 9:

(i) SEQUENCE CHARACTERISTICS:
        (A) LENGTH: 3506 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (vi) ORIGINAL SOURCE:
        (A) ORGANISM: Sus scrofa (ix) FEATURE:
        (A) NAME/KEY: misc_feature
        (B) LOCATION:2928..2929
        (D) OTHER INFORMATION:/label= n
            /note= ""n" stands for S"

(xi) SEQUENCE DESCRIPTION: SEQ ID NO: 9:

GATCTTTTTT TAAGAGAGTC TCATCTGACT GACACAGTCT GGGTAAGGTG CTGTGAGGAA          60

GCAGGGGGAT GCATAAACTG ACTTCTCCAG GCCCCTTCCA GCCTACACCT ACCCCTTCCT         120

TCTTCCCCCC CGCCTCACCC CCACCCCCAC TGGGCTTCTT TGGGACTGGC GAGTAGGCAG         180

GCCGCCCAGC TAGGAGTAAT TGAAAGGAGC AGATGAGAGG AGAATGTGTG TCCTCCCCCA         240

CCTCCCCAGC CCCCATGGGG GCTGCAGAGA AATGAAAACT AATCAAATTA CACCCTATGG         300

```
CCTCCTTACC CGTGCACAGG AGCCTGCTGG GGGCAGGCTG GCTGTGGGGA GGGGGGGTGC     360

AGGGGGAGAG GGAAGGGGAA TCACATCTAA TCCACTGTAA ACGTCTTGAT GTGCAGCAAC     420

AGCTTAGAGG GGGGCTCAGG TTTCTGTGGC GTTGGCTATA TTTATCTCTG GTTCCATGCC     480

AGCGGGAGG GTTTAAATGG CACCCAGCAG TTGGCGTGAG GGGCTGCAGG AGCTTGGGGG      540

CTGGTGGCAG GAACAAGTCT TTTCTGACCC CATGGAGCTG TATGAGACAT CCCCCTACTT    600

CTACCAGGAA CCCCACTTCT ATGACGGGA AAACTACCTG CCCGTCCACC TCCAGGGCTT     660

TGAGCCACCA GGCTACGAGC GGACTGAGCT GAGTCTGAGC CCTGAGGCCC GAGTGCCCCT    720

GGAAGATAAG GGGCTGGGGA CCCCCGAGCA CTGCCCAGGC CAGTGCCTGC CGTGGGCATG   780

TAAGGTGTGT AAGAGGAAGT CCGTGTCTGT GGACCGTCGG CGGGCCGCCA CGCTGAGGGA   840

GAAGCGCAGG CTCAAGAAGG TGAATGAGGC CTTTGAGGCC CTGAAGAGGA GCACCCTGCT   900

CAACCCCAAC CAGCGGCTGC CCAAGGTGGA GATCCTGCGC AGCGCCATCC AGTACATCGA   960

GCGCCTGCAG GCCCTGCTCA GCTCCCTCAA CCAGGAGGAG CGAGACCTCC GCTACCGAGG  1020

CGGGGGCGGG CCGCAGCCAG GGGTAAGTGG CTGTCCCACC CCCCTGCCCT GGGGCGGGG    1080

GCACAGGAGG CACCCAGACA GCCTCGGGGA CCCCATGGTG GGGCTCGGTC AGATGGATGA  1140

ACAGGAGCCA GGCAGGGTCT GAGAAGGCTT CAAGGTGCCT GCCTTTGTTA GAGCGGGGCT  1200

GCCCAGCTGA CCTCCTGCGT CACCGTGTCC TTTTCAGATA AGATGAAGGC AGTGGGGAGA  1260

AGCGTGTGGA GGGGGTGGGT GGCACAGGAC CGAAGGAAGG ATCCAGGAGC AAGTCCAGAT   1320

GGAGCTGGAT GAGGGAGAAG ATTCACCCCG TGTCTGGGGA CAGGGCCTAA AAGGCAAGGC  1380

CAAATGTCCC TGAGAAGACT GCTTTTCCCC TCACCCGACC CCATCTTGGG TATGGCTGAC   1440

AGAAAGAAAA CCCACCCAGT CTCTCGCATG ACACCTGCAC AAAAGTGGCC CTGGTTTGGC   1500

TGGACATTCT GCCTCCTTCA TTCTGCCTCC TTATCCCAGG GTCAGGAAAC CACAGACCCC    1560

CTTAAGCTGA GTGTCCTGTG AGGACAGAAT TGCCACCCAG AATGGATGCT AGGAAAGGCC  1620

TTGAAGCAGG GGTTCTGTGG CCTGACAGAG GCATTGAAAG GAGCTGATTT TGAAGATTCT  1680

GGAATAGGAG GTGGGCTGGA CTGGATGGTT CAGACTGTGG TCCACCTTCC AACCCCACCA  1740

CAGGTGCTTC TGCCCATTGG AACGAGACAA AGAGACACTG CTAAGAACAG CGGAGCCCTG  1800

ACCTTGGGCC TTCACCCTAT CTTGCAGGTG CCCAGTGAAT GCAGTTCCCA CAGCGCCTCC  1860

TGCAGTCCAG AATGGGGCAG TGCACTGGAG TTCGGCCCCA ACCCAGGGGG TAAGTGAGGC  1920

CAGGACCCTG GTTACCTTGA CTCAAGTCCC ACAGTCTATC TGTAGGTCCA GTTCTCCCCT   1980

CTTACCTTAC ACCCTGCTCC AGTCCTCTTC CCTTGGCCTC TCTAGGGACC TCTTGAACCC  2040

TGGGCCACAA ACAGTGAGCT AGGAGGCCCG GTGCCTCCCT GAAGCCTTGA CCAGCTAAGG  2100

AGTAGTCTAG GTCTCCTGCA GCTCCCCAGT TGGTGCCTGA TGGCTGACCT TCCCCACGGA   2160

GAGGATAATG TCCCTGCCCA GGGGTCCCT GGGAATTGCT GAGTCAGGGC TGCAAAACTG     2220

GTACCGCAAA GGGCAGTTCC GGTTTCCCAG GATACACCAC TCTGGCTCCA CCTAGGAATA  2280

GCTGCTTCCA AATTCTAACC CCAGCAGGGG ATTTCCGAGA GGACATACTT GCATTCTCTC  2340

TCTCTCTCAC ACACACACAA TCACGTGCAT ATAGCATCGG GAAAAGCATG GGCCGGGAA    2400

AAGGACTCTG AGCTTTTCTC ACCCATCTGT CCTGGAAAAC CTGTGCCACT TCAAAGAGCT  2460

CAGCCTCTGC CTTGAGTCTT GAGACCCTTT CATTACCCAG GTAACATCTT TCTACCTTCT  2520

CCTTACAGAT CATCTGCTCA CAGCTGACCC TACAGATGCC CACAATCTGC ACTCCCTCAC  2580

CTCCATCGTG GACAGCATCA CAGTGGAGGA TGTGGCTGTG GCCTTCCCAG ATGAAACCAT   2640

GCCCAACTGA GACTGTCTGC CAGGATGGGT GTGCGTGAGA GCCCCCCCCA AGGCTGGCCA  2700
```

```
CAGACGGCAC CACTTCTGCA GCAGGGCTCT CCTAAGCCAG TTGTCCTGCT GCCAGGAAGC    2760

CAGCCCTGGG GTTGCCAAAT GCCAGACTAA CCCCCTCCTC ATCCATATAA GGTTAGCCCA    2820

CCACCCAGAG AGGGAATGGA TGCTCTCATT TATCTGACTC CTTAGAGCAG AAAGCAGTTC    2880

TGTTTCCAAG GGGATAAAAC AGGGGACCAG AGTGCCCCCT TGCGTAANCC CCTGGCTCAG    2940

GGACAAACTC AGGAGCTTCC CTTTGATCAT AATGCAGCCT TCAATTCCAC CCCCTAAAAA    3000

GAAACAGTTT GAGAGACGAA GAGTGTCTTG ACCTGGACAA GCTATGCACA TCTCCTGTTC    3060

GTGTCTCTTC CTAAGCCAGT GGCTAGGCTG GGCTGCCTGA ATTGAGAGAA GAAAAGGAGA    3120

GGAACAATCC TCTATTCCCA AGTCCCTGGG GGGCCAAGCT TTTGCAGTGA ATATTGGGAA    3180

ACTTCCAGTG GTTTTATGTT TTGTTTTGTG TGTTGTTTGT AAAGCTGCCA TCTGACCAAG    3240

TTCTCTTGTG CTGAAGTTGC CAGGGACAGG CGGGGGGGTG GGGGTGGGGT GGGGGGCAGG    3300

GGCTCCTGGG GTGATTTGTT AACTAAGCAT CGTGTGGTTT TGCCATTGTT TTATATATTT    3360

TTTGCTAACT TATTTGGATT TCTTTTTTAA AAAATGAATA AAGACTGGGT GCTAGAGGAG    3420

TGTCTGTAAT GATATAGAGG GAGGAGATGA CTGCTGCTAT AGGCTCTTCC ACCTAAGTGG    3480

TCCAGACCCA TCCAAGGGGC AGGGCT                                        3506
```

(2) INFORMATION FOR SEQ ID NO: 10:

(i) SEQUENCE CHARACTERISTICS:
        (A) LENGTH: 224 amino acids
        (B) TYPE: amino acid
        (C) STRANDEDNESS: single
        (D) TOPOLOGY: linear     (ii) MOLECULE TYPE: peptide     (iii) HYPOTHETICAL: NO     (xi) SEQUENCE DESCRIPTION: SEQ ID NO: 10:

```
Met Glu Leu Tyr Glu Thr Ser Pro Tyr Phe Tyr Gln Glu Pro His Phe
 1               5                  10                  15

Tyr Asp Gly Glu Asn Tyr Leu Pro Val His Leu Gln Gly Phe Glu Pro
            20                  25                  30

Pro Gly Tyr Glu Arg Thr Glu Leu Ser Leu Ser Pro Glu Ala Arg Val
        35                  40                  45

Pro Leu Glu Asp Lys Gly Leu Gly Thr Pro Glu His Cys Pro Gly Gln
    50                  55                  60

Cys Leu Pro Trp Ala Cys Lys Val Cys Lys Arg Lys Ser Val Ser Val
65                  70                  75                  80

Asp Arg Arg Arg Ala Ala Thr Leu Arg Glu Lys Arg Arg Leu Lys Lys
                85                  90                  95

Val Asn Glu Ala Phe Glu Ala Leu Lys Arg Ser Thr Leu Leu Asn Pro
            100                 105                 110

Asn Gln Arg Leu Pro Lys Val Glu Ile Leu Arg Ser Ala Ile Gln Tyr
        115                 120                 125

Ile Glu Arg Leu Gln Ala Leu Leu Ser Ser Leu Asn Gln Glu Glu Arg
    130                 135                 140

Asp Leu Arg Tyr Arg Gly Gly Gly Gly Pro Gln Pro Gly Val Pro Ser
145                 150                 155                 160

Glu Cys Ser Ser His Ser Ala Ser Cys Ser Pro Glu Trp Gly Ser Ala
                165                 170                 175

Leu Glu Phe Gly Pro Asn Pro Gly Asp His Leu Leu Thr Ala Asp Pro
            180                 185                 190
```

```
-continued

Thr Asp Ala His Asn Leu His Ser Leu Thr Ser Ile Val Asp Ser Ile
            195                 200                 205

Thr Val Glu Asp Val Ala Val Ala Phe Pro Asp Glu Thr Met Pro Asn
        210                 215                 220
```